United States Patent
Schlapfer et al.

(10) Patent No.: US 7,841,798 B2
(45) Date of Patent: Nov. 30, 2010

(54) DEVICE FOR A BALL-AND-SOCKET TYPE JOINT CONNECTION OF TWO MEMBERS

(75) Inventors: Fridolin Schlapfer, Glarus (CH); Renzo Defranceschi, Ramlinsburg (CH)

(73) Assignee: Synthes USA, LLC, West Chester, PA (US)

( * ) Notice: Subject to any disclaimer, the term of this patent is extended or adjusted under 35 U.S.C. 154(b) by 1080 days.

(21) Appl. No.: 11/582,573

(22) Filed: Oct. 16, 2006

(65) Prior Publication Data

US 2007/0032849 A1    Feb. 8, 2007

Related U.S. Application Data

(63) Continuation of application No. 10/881,166, filed on Jun. 30, 2004, now Pat. No. 7,121,755, which is a continuation of application No. PCT/CH01/00744, filed on Dec. 31, 2001.

(51) Int. Cl.
*A61F 2/44*    (2006.01)
(52) U.S. Cl. .................... 403/77; 403/90; 403/123; 403/399; 623/17.11; 623/17.14; 606/250
(58) Field of Classification Search ............. 403/7, 403/90, 123, 398, 399, 77; 606/246, 247, 606/250, 279, 300; 623/17.11, 17.14
See application file for complete search history.

(56) References Cited

U.S. PATENT DOCUMENTS 5,443,467 A    8/1995    Biedermann et al.
5,466,237 A    11/1995   Byrd, III et al.
5,733,286 A    3/1998    Errico et al.
6,063,090 A    5/2000    Schläpfer
6,086,588 A    7/2000    Ameil et al.
6,440,137 B1   8/2002    Horvath et al.
6,540,748 B2   4/2003    Lombardo
6,582,436 B2   6/2003    Schläpfer et al.
6,610,063 B2   8/2003    Kumar et al.
6,626,908 B2   9/2003    Cooper et al.
6,663,635 B2   12/2003   Frigg et al.
7,121,755 B2 * 10/2006   Schlapfer et al. ............. 403/77

FOREIGN PATENT DOCUMENTS

FR    2810533       12/2001
WO    WO 01/22893   4/2001

* cited by examiner

*Primary Examiner*—Michael P Ferguson
(74) *Attorney, Agent, or Firm*—Stroock & Stroock & Lavan LLP

(57) ABSTRACT

A device for a ball-and-socket-type connection of two members includes a first member having a head and a second member having a cavity that receives the head. The cross-sectional surface of the cavity is tapered at the lower end of the second member as a result of a constriction. The head and/or cavity is configured spherically with a center of articulation (Z). The ball-and-socket-type connection between the two members can be detachably fixed by means of a clamping element that can be connected to the second member. The head has a recess in which the front end of the clamping element can rest. The recess and/or the front end has an at least partially spherical surface with a center (C). In the clamped position of the device, the center of articulation (Z) and the center (C) are identical.

8 Claims, 7 Drawing Sheets

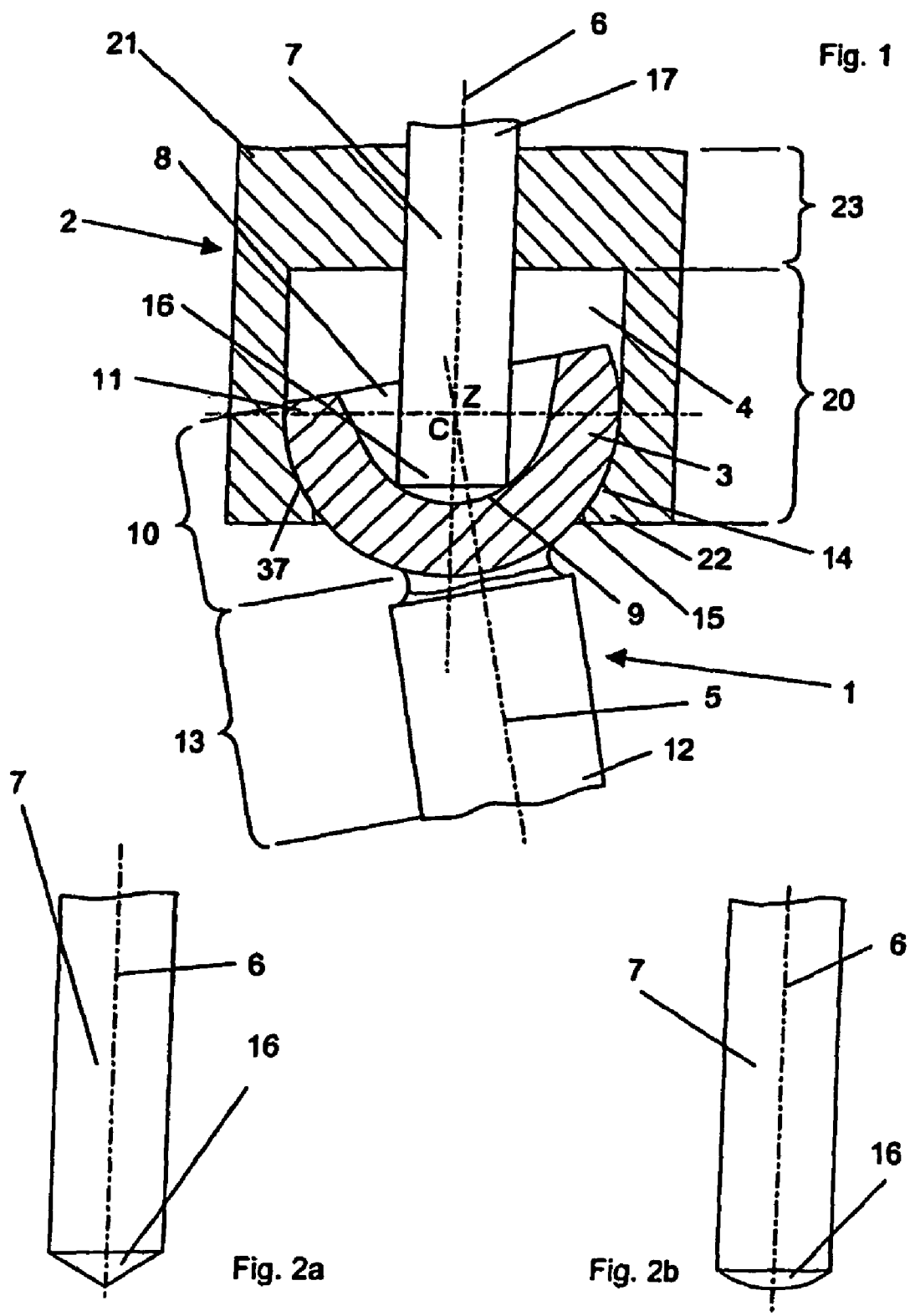

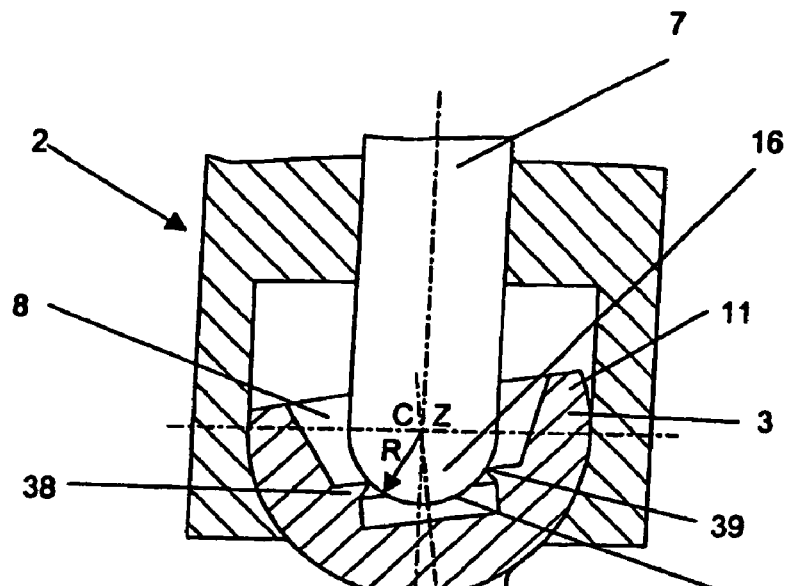
Fig. 3
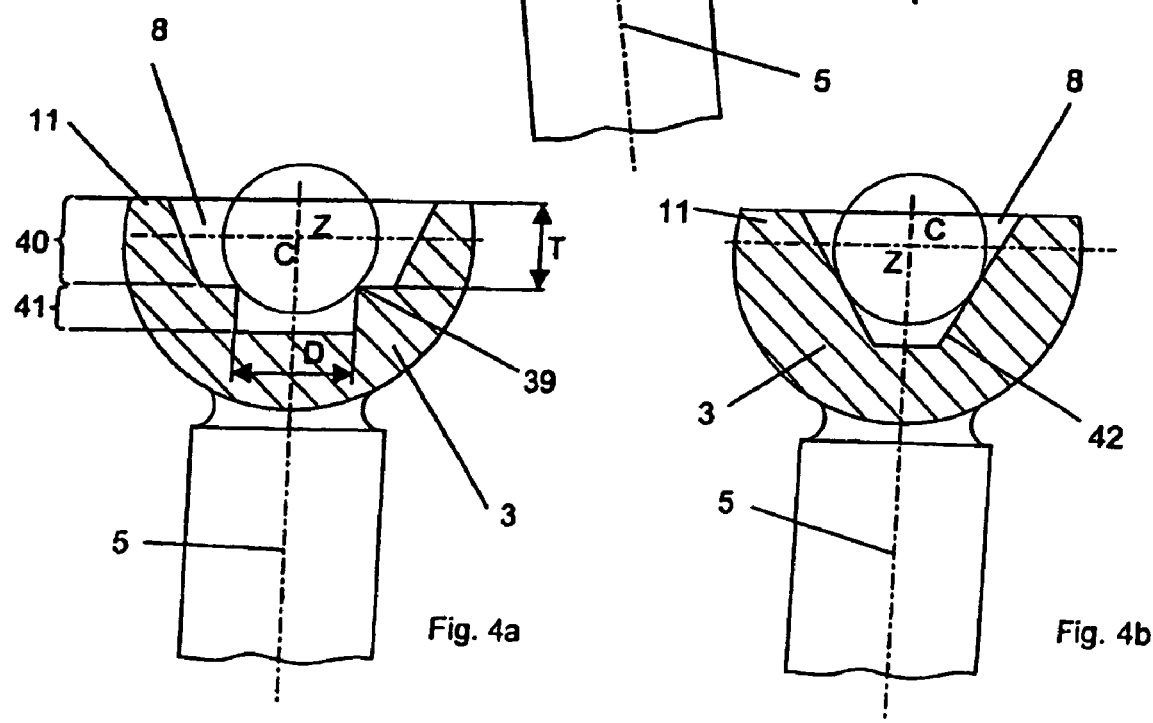
Fig. 4a
Fig. 4b

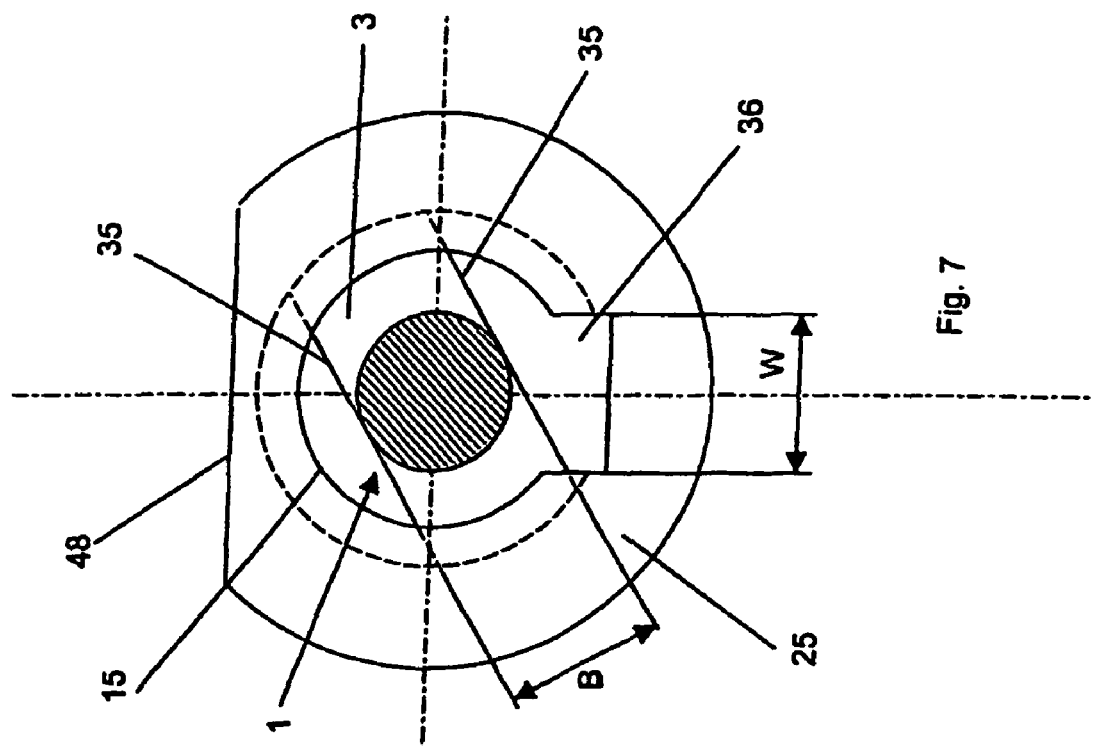
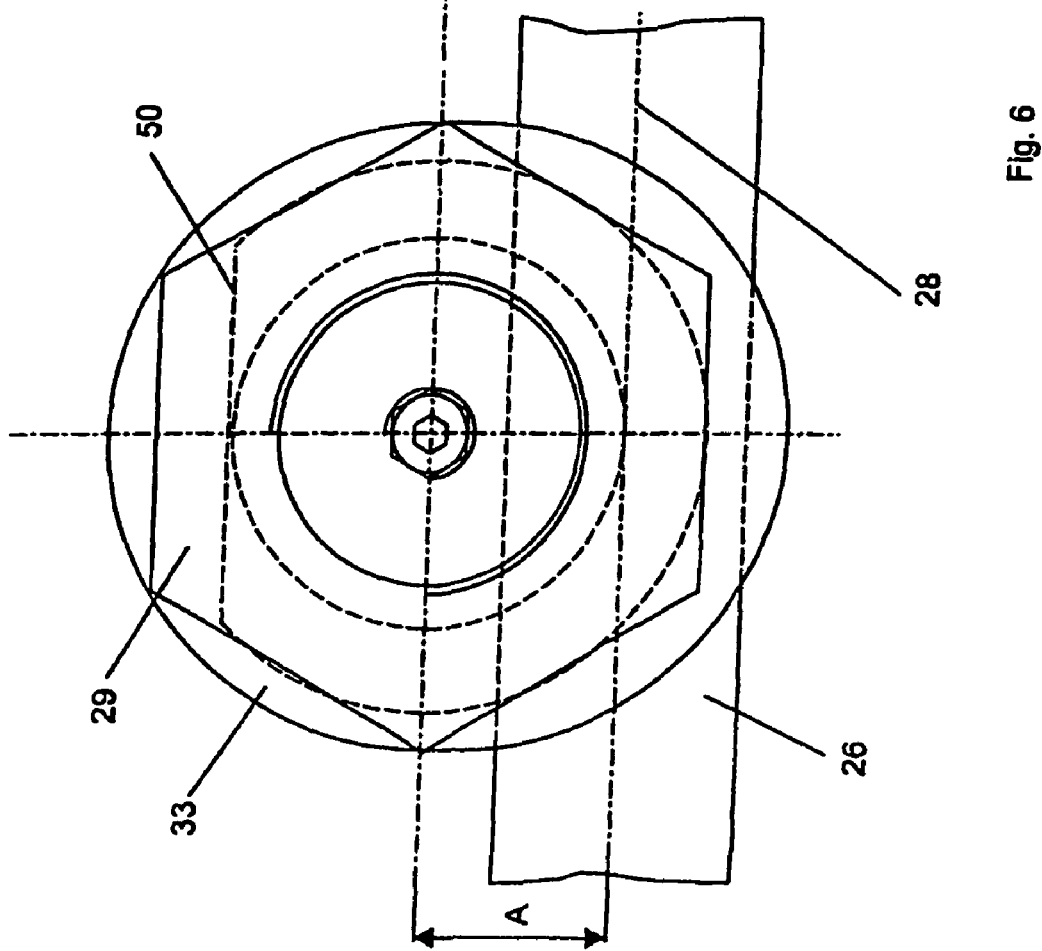

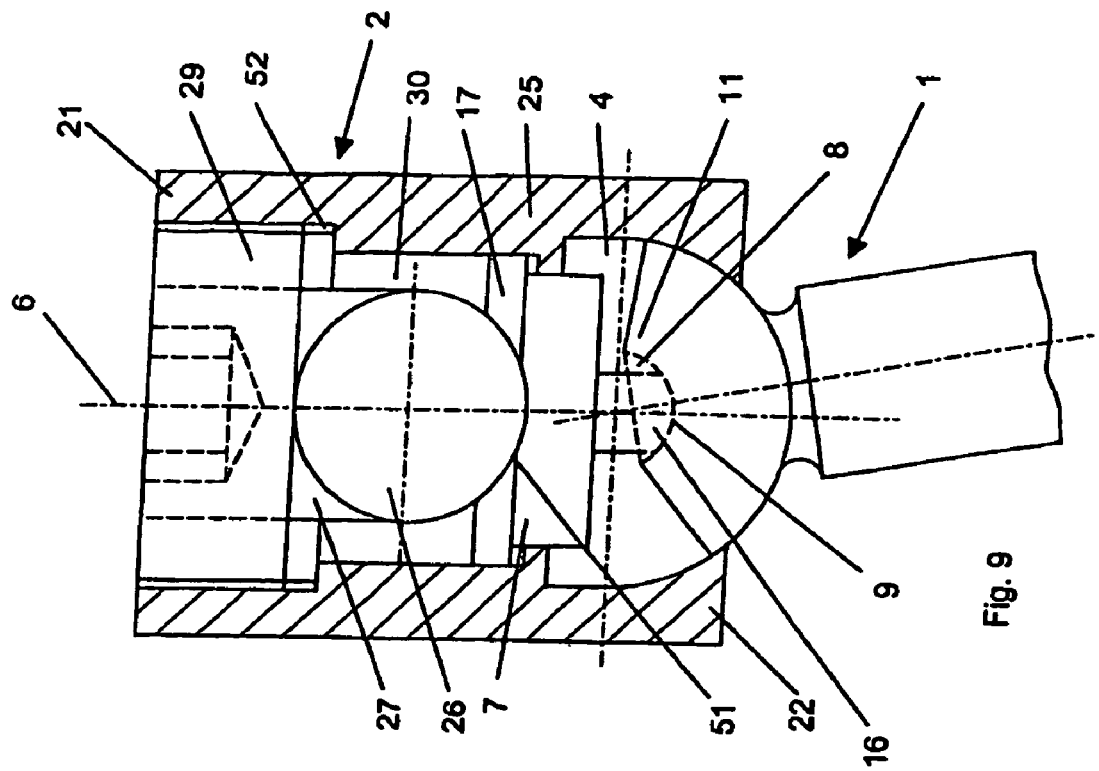
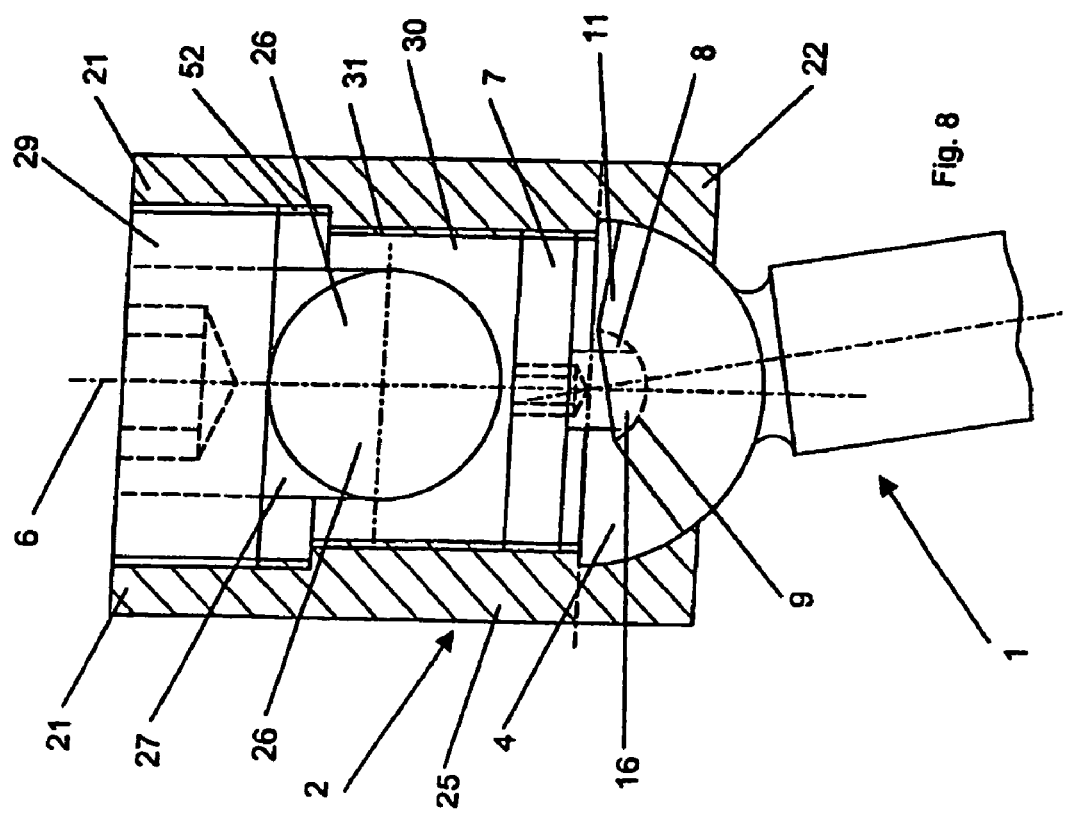

DEVICE FOR A BALL-AND-SOCKET TYPE JOINT CONNECTION OF TWO MEMBERS

CROSS-REFERENCE TO RELATED APPLICATIONS

This is a continuation of U.S. patent application Ser. No. 10/881,166, filed Jun. 30, 2004, now U.S. Pat. No. 7,121,755, which is a continuation of International Patent Application No. PCT/CH2001/000744, filed Dec. 31, 2001, the entire contents of both are expressly incorporated herein by reference thereto.

FIELD OF THE INVENTION

The invention relates to a device for the ball-and-socket type joint connection of two parts.

BACKGROUND OF THE INVENTION

A stabilization device that interconnects the bone-fixation means, such as pedicle screws, with a longitudinal member, such as a longitudinal spinal rod, extending along at least a portion of a patient's spinal column, is used, for example, for the internal stabilization of the spinal column. In order to securely stabilize the spinal column, it should be possible to connect the bone-fixation means, on the one hand, firmly with the vertebrae and, on the other, with the longitudinal member. Preferably, the head of the bone fixation means and the longitudinal member are connected by a connecting mechanism, which permits the longitudinal member to be fixed with respect to the bone-fixation means at a variety of different angles. Moreover, the connecting mechanism may be detachable, so that the mechanism may be later removed without large openings being formed in the tissue of the spinal column.

Such a connection mechanism between a bone-fixation means and a longitudinal member for the internal stabilization of a vertebrae is known, for example, in U.S. Pat. No. 5,466,237 to Byrd which discloses a bone-fixation screw having a screw head, which is constructed with a spherical shaped lower surface and a convexly shaped upper surface. The spherical shaped lower surface is mounted in a borehole formed in the connecting mechanism, this borehole comprising a concave section, which tapers towards the screw shaft, as a result of which, and together with the screw head, a ball-and-socket type joint connection is established between the bone-fixation screw and the connecting mechanism. This connection is locked by tightening a nut, which can be screwed over an external thread formed on the upper portion of the connecting mechanism. Tightening the nut, forces the nut against the longitudinal member, which is placed in a transverse channel formed in the connecting mechanism for this purpose. The longitudinal member thereafter presses on the convexly-shaped upper surface of the bone-fixation screw, so that, as the nut is tightened, the longitudinal member and the bone-fixation screw are locked in the connecting mechanism.

A bone-fixation screw having a screw head with a spherically shaped lower surface is also disclosed in International Publication No. WO 01/03593 to Frigg (corresponding to U.S. Pat. No. 6,663,635), which discloses that the center of the spherical lower surface and the spherical upper surface can be spaced apart or coincide with respect to the longitudinal axis of the bone-fixation screw.

Another device for connecting a bone-fixation screw with a longitudinal member, which permits limited, separate locking of the longitudinal member and the bone-fixation screw, is disclosed in German Publication No. DE 43 07 576 to Biedermann (which corresponds to U.S. Pat. No. 5,443,467).

One disadvantage of the connecting mechanism in these known devices is that the connecting mechanism must have a generally large, overall height.

A device for connecting a bone-fixation screw with a longitudinal member, which permits a lower overall height due to the configuration of the joint connection and its locking mechanism, is disclosed in International Publication No. WO 01/22893 to Lombardo which discloses a bone-fixation screw having a screw head with a partially lower spherical surface and a top surface having a coaxial, conical cavity for receiving a convexly formed front end of the clamping means which accommodates polyaxially movement and which may be pressed by mounting means against the conical wall of the cavity. The mounting means can be screwed coaxially into the connecting mechanism at the upper end of the connecting mechanism and, when the device is locked, press against the longitudinal member, which is inserted in the transverse channel formed in the connecting mechanism, which in turn, presses on the clamping means. One disadvantage with this device is that, because the convex, front end of the clamping means is pressed into the conical cavity at the screw head of the bone screw, there is a wedging effect which creates a levering force, which aligns the bone screw parallel with the central axis of the connecting mechanism.

Thus, there remains a need for a connecting mechanism that provides a reduced overall height and which overcomes the problems associated with the prior art.

SUMMARY OF THE INVENTION

The present invention addresses these problems and others by providing a device, which comprises a spherically shaped connection between two members, the mechanism comprising clamping means, the front end of which contacts the surface of a depression formed in the joint head of the bone-fixation means, as a result of which a smaller overall height of the connection mechanism is possible, and which, in the unlocked state, permits polyaxially angular position of the central axes of the two parts relative with respect to each another.

Pursuant to the invention, this objective is accomplished with a device for the ball-and-socket type connection of two members. The advantages, achieved by the invention, are a result of the fact that:

due the coincidence of the center of the joint and of the center of the spherically shaped contact surface at the front end of the clamping means and/or of the depression at the joint head, locking of the two members with respect to one another at different angles of the central axes of the two members becomes possible without the occurrence of levering forces associated with the prior art; and because the joint head is fixed in the cavity by the clamping means, the front end of which can be brought into contact with a depression at the joint head, the latter can be configured lower, as a result of which the device has smaller dimensions.

As will be described herein, the clamping means in various, different embodiments can be configured differently at their front end, depending on the desired form of contact with the depression, for example:

by configuring the front end of the clamping means as a point, which is concentric with the central axis, a punctiform contact between the front end and the depression can be achieved;

by configuring the front end of the clamping means as a flattened surface, orthogonally to the central axis, linear contact between the front end and the depression can be attained and by configuring the front end of the clamping means spherically, a contact surface can be established between the front end and the depression.

In further embodiments, the depression formed in the joint head of the bone-fixation means may be spherical or conical, as a result of which, by pairing clamping means with a spherically formed front end, a contact surface or a linear contact can be attained between the front end of the clamping means and the depression.

In further embodiments, the depression is provided with a circular edge, which is concentric with the central axis and, together with the spherically configured front end of the clamping means, also forms a linear contact.

Preferably, the joint head of the bone-fixation means may be constructed rigidly, so that no expansion of the joint head is possible when the device is locked.

In a preferred embodiment of the invention, the device may include:

a) a first member whish is sized and configured as a bone-fixation means, for example, as a pedicle screw, a pedicle hook, etc., the lower segment of which is used to fix the bone-fixation means to a patient's bone; and b) a second member which is sized and configured as a connecting mechanism and/or part for interconnecting the longitudinal member, for example, a longitudinal spinal rod, with the bone-fixation means. The second member may further include a channel, disposed transversely to the central axis, for accommodating the longitudinal member and a central borehole with internally formed threads, disposed coaxially with the central axes.

Furthermore, the device may include mounting means for fixing the longitudinal member, inserted into the transverse channel, so that the device can be used, for example, as a spinal fixation device.

The clamping means may directly lock and/or unlock, and may be in the form, for example, of a clamping screw, which may threadedly engage, for example, the internal threads formed in the central borehole of the connecting member. By this, it becomes possible that the locking and/or unlocking of the bone-fixation means by means of the clamping screw in the connecting member can take place independently of the locking and/or unlocking of the longitudinal member by means of the clamping means.

On the other hand, the clamping means may indirectly lock and/or unlock, and coaxially move within the central borehole formed in the connecting member and, for example, may be locked and/or unlocked by means of a mounting means.

Alternatively, the transverse channel may open toward the side of the device, i.e., a side-loading pedicle screw. The side-loading pedicle screw may also include a covering cap, which may be pushed over the connecting member parallel to the central axis. The covering cap may include a tab formed parallel to the central axis, the tab enabling the channel opening to be closed when the mounting means is tightened, thereby clamping the longitudinal member inside the channel between the wall of the channel and the tab. In this embodiment, with respect to the central axis, the channel preferably is offset from the channel opening so that it becomes possible that the clamping screw may be screwed into the connecting member adjacent to the channel, so that, in comparison to the previous embodiments, the clamping screw can be screwed into the connecting member below the channel, thereby reducing the overall height of the connecting member even more.

In yet another, different embodiment of the invention, the channel may be configured at the upper end of the connecting member, i.e., a top-loading pedicle screw. The mounting means may be pressed directly onto the longitudinal member, so that the longitudinal member can be fixed in the channel by means of the clamping means.

In a further embodiment of the invention, the joint head of the bone-anchoring means may include two flat spots, which are parallel to the central axis and which are separated by a distance B from one another, wherein the connecting member further includes a groove, provided parallel to the central axis, having a width W. The groove providing an enlarged opening of the cavity at the lower end of the second member perpendicularly to the width W in such a manner, that the joint head, with the flat spots parallel to the side walls of the groove, can be introduced into and removed from the cavity starting from the lower end of the second member. On the other hand, when the flat spots are rotated with respect to the side walls of the groove, the joint head, due to the support in the cavity, is secured axially against the lower end of the second member.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein:

FIG. 1 shows a longitudinal section through an embodiment of the inventive device, FIG. 2a shows a section of the clamping means of an embodiment of the inventive device, FIG. 2b shows a section of the clamping means of a different embodiment of the inventive device, FIG. 3 shows a longitudinal section through a further embodiment of the inventive device, FIG. 4a shows a section through the joint head of an embodiment of the inventive device, FIG. 4b shows a section through the joint head of a different embodiment of the inventive device, FIG. 6 shows a view from above of the embodiment of the inventive device, shown in FIG. 5, FIG. 7 shows a view from below of the embodiment of the inventive device, shown in FIGS. 5 and 6, FIG. 8 shows a section through a further embodiment of the inventive device, FIG. 9 shows a section once again through a further embodiment of the inventive device.

DETAILED DESCRIPTION OF THE INVENTION

Figure 5:
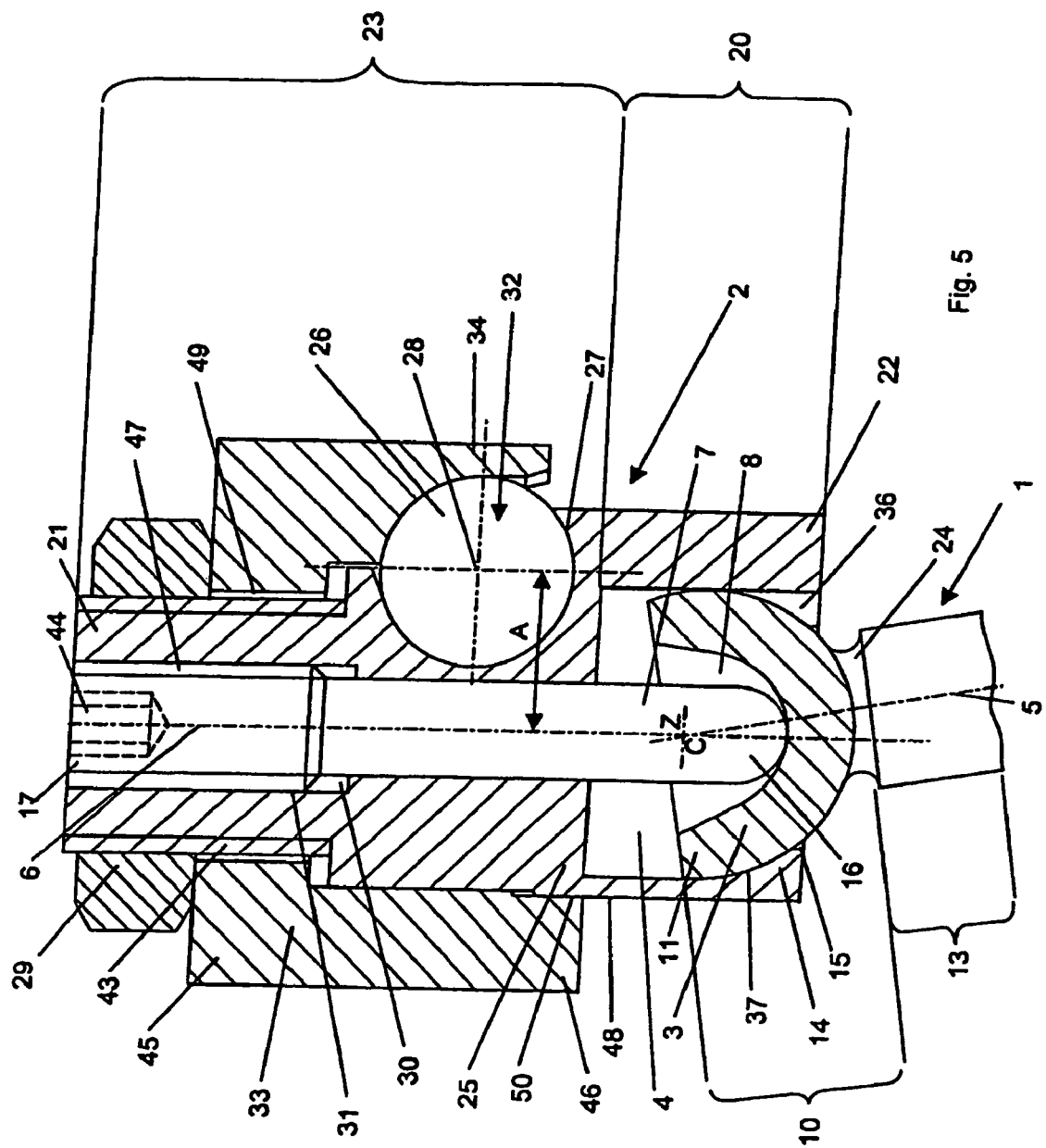
FIG. 5 shows a section through a further embodiment of the inventive device.

For the purposes of promoting an understanding of the principles of the invention, reference will now be made to an exemplary, non-limiting embodiment illustrated in the figures and specific language will be used to describe the same. It will nevertheless be understood that no limitation of the scope of the invention is hereby intended, such alterations and further modifications, and such further applications of the principles of the invention as illustrated herein being contemplated as would normally occur to one skilled in the art to which the invention relates.

As shown in FIG. 1, the device includes a first member 1 and a second member 2, wherein the second member 2 includes a cavity 4 and clamping means 7 while the first member 1 has a central axis 5, an upper end 11, and a lower end 12. The upper end 11 of the first member 1 may include a first joint segment 10, which may be constructed as a spherically shaped joint head 3, the center of which, preferably lies on the central axis 5 and forms a center of joint Z. As shown, the joint head 3 may be flattened at the upper end 11 of the first member 1. Furthermore, the joint head 3 may include a depression 8, which may be partly spherical with a spherical shaped surface 9 and which terminates conically into the upper end 11 of the first part 1. The spherical shaped surface 9 of the depression 8, having a center C, which preferably is constructed so that center C lies on the central axis 5 and coincides with the center Z.

The second member 2 may also have a central axis 6, an upper end 21, a lower end 22, an upper segment 23 and a cavity 4, which is disposed at the lower end 22 and forms the second joint segment 20. The cavity 4 may be disposed coaxially with the central axis 6 and is tapered at the lower end 22 of the second member 2 by a constriction 14 formed on the lower end 22. Preferably, the constriction 14 has a spherical shaped support 37 forming a center which coincides with the joint center Z. The spherically shaped support 37 being directed towards the interior of the cavity 4. Preferably, the spherically shaped support 37 is complementary with the surface of the joint head 3, so that the two joint segments 10; 20 can be rotated with respect to one another about three mutually perpendicular axes.

As shown, at the lower end 22 of the second member 2, the cavity 4 may have an opening 15, which may be coaxial with the central axis 6 and through which the lower segment 13 of the first member 1 can pass.

The clamping means 7 may be disposed coaxially with the central axis 6 of the second member 2. The clamping means 7 may include a front end 16 and a rear end 17 which are preferably disposed so that they may be displaced coaxially with the central axis 6. The front end 16 of the clamping means 7 may be constructed circularly cylindrically and may be brought into contact with the spherically shaped surface 9 of the depression 8. By pressing the front end 16 onto the spherically shaped surface 9 of the depression 8, the joint head 3 can be locked in the cavity 4 formed in the second member 2. The first and second members 1, 2 with the polyaxially angular arrangement of their central axes 5, 6 being lockable because of the identity of location of the center C of the spherically shaped surface 9 of the depression 8 with the joint center Z.

As shown, in FIGS. 2a and 2b, in each case showing different embodiments of the clamping means 7, the front end 16 of the clamping means 7, as shown in FIG. 2a, may have a point which is coaxial with the central axis 6, whereas, as shown in FIG. 2b, the front end 16 of the clamping means 7 is shown as being convexly spherical.

The device, as shown in FIG. 3, differs from the embodiment, shown in FIG. 1, only in that the depression 8 in the joint head 3 and the front end 16 of the clamping means 7 are constructed differently. As shown, the front end 16 of the clamping means 7 is hemispherical with the center C lying on the central axis 6, and has a radius R. While the depression 8 is conical with an annular elevation 38, which is concentric with the central axis 6. The elevation 38 has a circular, sharp edge 39, which is directed towards the interior of the depression 8. The axial distance between the edge 39 and the upper end 11 of the first part 1 and the diameter of the circular edge 39 are such that the edge 39 lies on an imaginary spherical surface with the center C lying on the central axis 6 and with the radius R.

As shown in FIG. 4a, the joint head 3 differs from the embodiments described above only in that the depression 8 at the upper end 11 of the first member 1 has a conical, coaxial section 40 and an axially adjoining circular cylindrical section 41 with the diameter D at a depth T, measured from the upper end 11. The diameter D is selected so that the depression 8 is constricted at the depth T by the circular cylindrical section 41, so that a circular edge 39, concentric with the central axis 6, is formed by the transition between the conical section 40 and the circular cylindrical section 41. Furthermore, the diameter D and the depth T are dimensioned so that the circular edge 39 coincides on an imaginary spherical surface with the center C, lying on the central axis 6, and with the radius R, as was the case with the embodiment depicted in FIG. 3.

As shown in FIG. 4b, the joint head 3 may have a conical depression 8 forming a cone 42. The diameter of the cone 42 at the upper end 11 of the first member 1 and the conical angle of the cone 42 are dimensioned so that the cone 42 touches an imaginary spherical surface with the center C, lying on the central axis 6, and with a radius R, as was the case with the embodiment depicted in FIG. 3.

A linear contact between the clamping means 7 and the depression 8 can be achieved by a configuration of the depression 8 and of the front end 16 of the clamping means 7 of one of the FIGS. 3, 4a or 4b.

As shown, in FIGS. 5-7 and 10, an alternate embodiment of the present device is shown wherein the device comprises, a first member 1 having bone fixation means 24, which as shown is a pedicle screw, but which may also be a pedicle hook, etc., and a second member 2 having a connecting part 25 for connecting a longitudinal spinal member 26 to the bone fixation means 24. As partially shown, the bone fixation means 24 may include a lower threaded shaft segment 13 and a joint screw head 3. The lower surface side of the screw head, i.e., on the side facing the screw shaft, the screw head is preferably constructed with a partially spherically surface having a radius $R_2$, the center of the spherical lower surface, preferably lying on the central axis 6, forming the joint center Z.

The upper surface side of the joint head 3 preferably has a depression 8, which has a partially spherical surface 9 with a center C and a radius $R_1$. The partially spherical surface preferably terminating conically into the outer surface at the upper end 11 of the first member 1. Preferably, the center C coincides with the joint center Z, so that the screw head can be locked in the connecting part 25 in such a manner that the central axis 5 of the first member 1 and the central axis 6 of the second member 2 can polyaxially rotate with respect to each another.

As shown, the cavity 4 in the connecting part 25, serving as a second joint segment 20, preferably includes a constriction 14, which as shown is a spherical support 37 having a joint center Z so that the spherically configured screw head is mounted on the support 37 so that it can be rotated polyaxially about the joint center Z.

The device further includes a clamping means 7, which as shown in FIG. 5, may be clamping screw having a rear end 17 with an external thread 47 sized and configured to mate with complementary internal threads 31 formed on the central borehole 30 of the connecting part 25. The rear end 17 of the clamping means 7 also may include means 44 for accommodating a screwdriver, a hex-driver, etc. As shown, the front end 16 of the clamping means 7 is formed with a spherical tip for contacting the spherical surface 9 in the depression 8 at the screw head. Although other shaped tips are envisioned.

Figure 10:
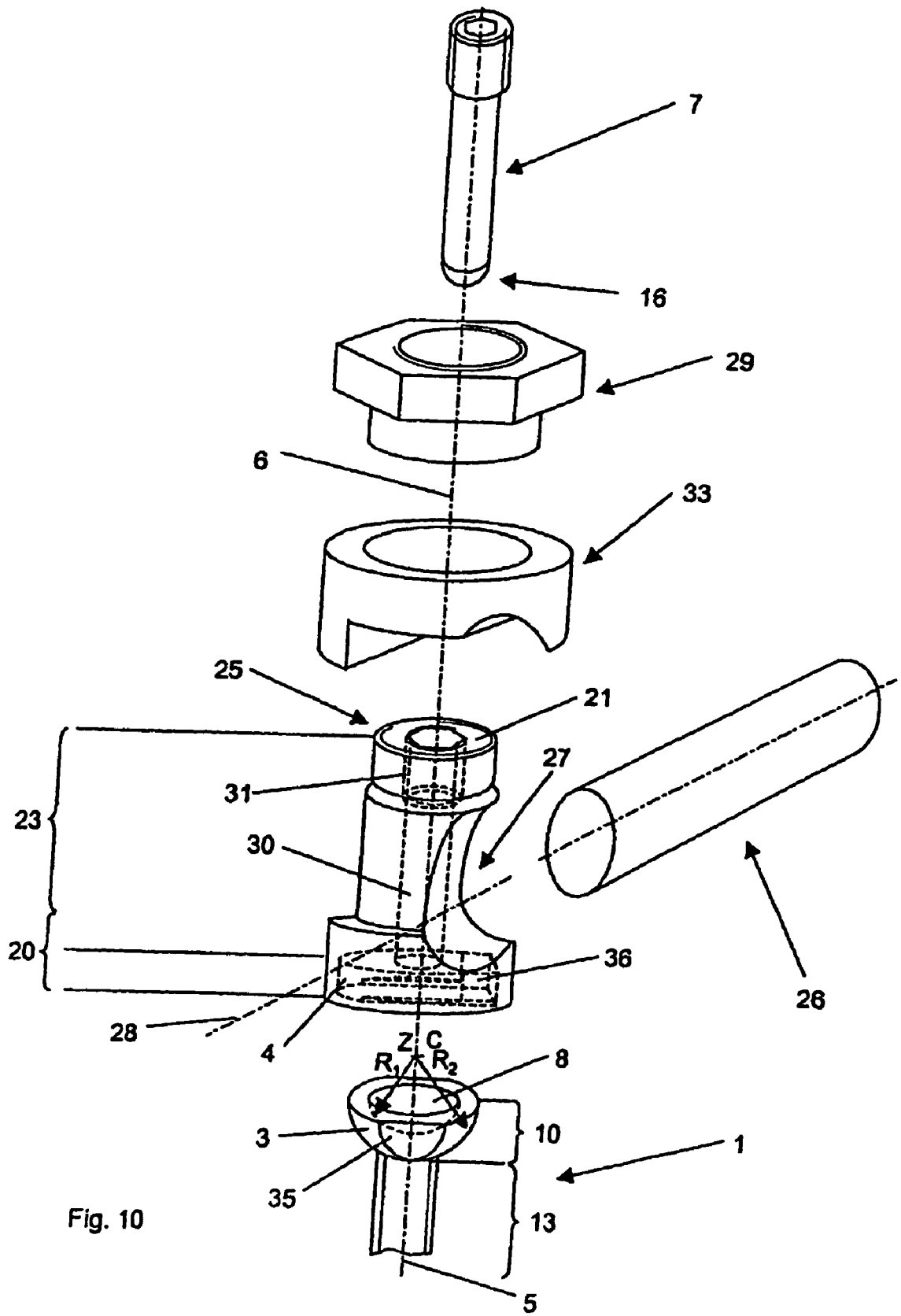
FIG. 10 shows an exploded representation of the embodiment of the inventive device shown in FIGS. 5, 6 and 7

As best shown in FIGS. 7 and 10, the joint head 3 may be equipped with two flat spots 35, which are preferably parallel to one another and to the central axis 5. The two flat spots 35 being separated by a distance B from one another. Similarly, the cavity 4 may include a groove 36 of width W, width W being greater than or equal to distance B, which is parallel to the central axis 6. The depth of the groove 36 is such that the opening 15 of the cavity 4 at the lower end 22 of the second member 2 is enlarged perpendicularly to the width B, so that the joint head 3 with the flat spots 35, parallel to the side walls of the groove 36, can be passed into or out of the cavity 4 from the lower end 22 of the second member 2 and then, by rotating the first member 1 about the central axis 5, the flat spots 35 at the joint head 3 are twisted with respect to the side walls of the groove 36, so that the joint head 3 can be fixed axially against the lower end 22 of the second member 2 by the constriction 14 formed in the cavity 4.

As shown, the device may further include a channel 27 for accommodating the longitudinal member 26, the channel being mounted in the connecting part 25 with the channel axis 28 extending transversely to the central axis 6. As shown, the channel 27 may be opened laterally at the connecting part 25 forming a channel opening 32 therein. The channel 27 is provided at the connecting part 25 so that the channel axis 28 is displaced by a distance A away from the central axis 6 towards the channel opening 32. A covering cap 33 is also provided, the cap 33 being placed coaxially on the central axis 6 over the connecting part 25 in order to fix the longitudinal member 26 in the channel 27. The covering cap 33 may include a tab 34, which is parallel to the central axis 6 and by means of which the channel opening 32 can be closed off by the covering cap 33 so that the longitudinal member 26 inserted into the channel 27 may be fixed in the channel 27. The covering cap 33 may be pressed coaxially along the central axis 6 by mounting means 29, which are shown herein as a nut which may threadedly engage the external threads 43 formed on the upper end 21 of the connecting part 25 so that the longitudinal member 26, inserted in the channel 27, can be fixed within the channel 27. Alternatively, the connecting member 25 may include internal threads for engaging an externally threaded nut.

Moreover, as shown, a device to prevent twisting can be mounted between the connecting part 25 and the covering cap 33. This device may be in the form of a flat spot 48 and a complementary constriction 50, the flat spot 48 being formed on a portion of the connecting part 25 extending parallel to the central axis 6 while the constriction 50 is formed on the central opening 49 of the covering cap 33, also extending coaxial with the central axis 6. So that when the covering cap 33 is pushed over the connecting part 25, the constriction 50 mates with the flat spot 48, so that twisting of the covering cap 33 about the central axis 6 with respect to the connecting part 25 is prevented.

As shown in FIG. 8, the device differs from the embodiment, shown in FIGS. 1 and 3, only in that the second member 2 may include a channel 27 formed in the connecting part 25 for accommodating a longitudinal member, the channel 27 being open at the upper end 21 of the connection part 25. The clamping means 7 may be screwed coaxially along the central axis 6 against the internal threads 31 formed in the central borehole 30 of the connecting part 25, so that the front end 16 of the clamping means 7 can be pressed against the surface 9 of the depression 8 at the upper end 11 of the first member 1. When the device is installed, the clamping means 7 is thus disposed between the longitudinal member 26 placed in the channel 27, and the cavity 4 in the second member 2. The longitudinal member 26 being locked in the channel 27 by mounting means 29, which is shown as an externally threaded setscrew and which, after the longitudinal member 26 is placed in the channel 27, can be screwed from the upper end 21 of the connecting part 25 into engagement with the internal threads 52. The internal thread 52 and the internal thread 31, both of which are disposed coaxially with the central axis 6 in the central borehole 30, can also be formed as a single internal thread.

As shown in FIG. 9, the device differs from the embodiment shown in FIG. 8 only in that the internal thread 52 formed in the central borehole 30 extends only so far from the upper end 21 of the connecting part 25, so that a longitudinal member 26 placed in the channel 27 can be locked in the channel 27 by means of the mounting means 29. As shown, the central borehole 30 is configured circularly cylindrically between the longitudinal section of the central borehole 30, which is provided with the internal thread 52, and the cavity 4, so that the clamping means 7 can be moved parallel to the central axis 6 in the central borehole 30. At its rear end 17, the clamping means 7 may include a notch 51, which extends transversely to the central axis 6. In the installed device, the longitudinal member 26, placed in the channel 27, rests in the notch 51, so that when the mounting means 29 is tightened, it presses against the longitudinal member 26, which in turn presses on the clamping means 7. The clamping means 7 thereafter being moved parallel to the central axis 6 against the front end 22 of the connecting part 25, thereby pressing with its front end 16 onto the surface 9 of the depression 8 at the upper end 11 of the first member 1. Thus, tightening the mounting means 29, locks the longitudinal member 26 and the first member 1 simultaneously in the device.

Figure 11:
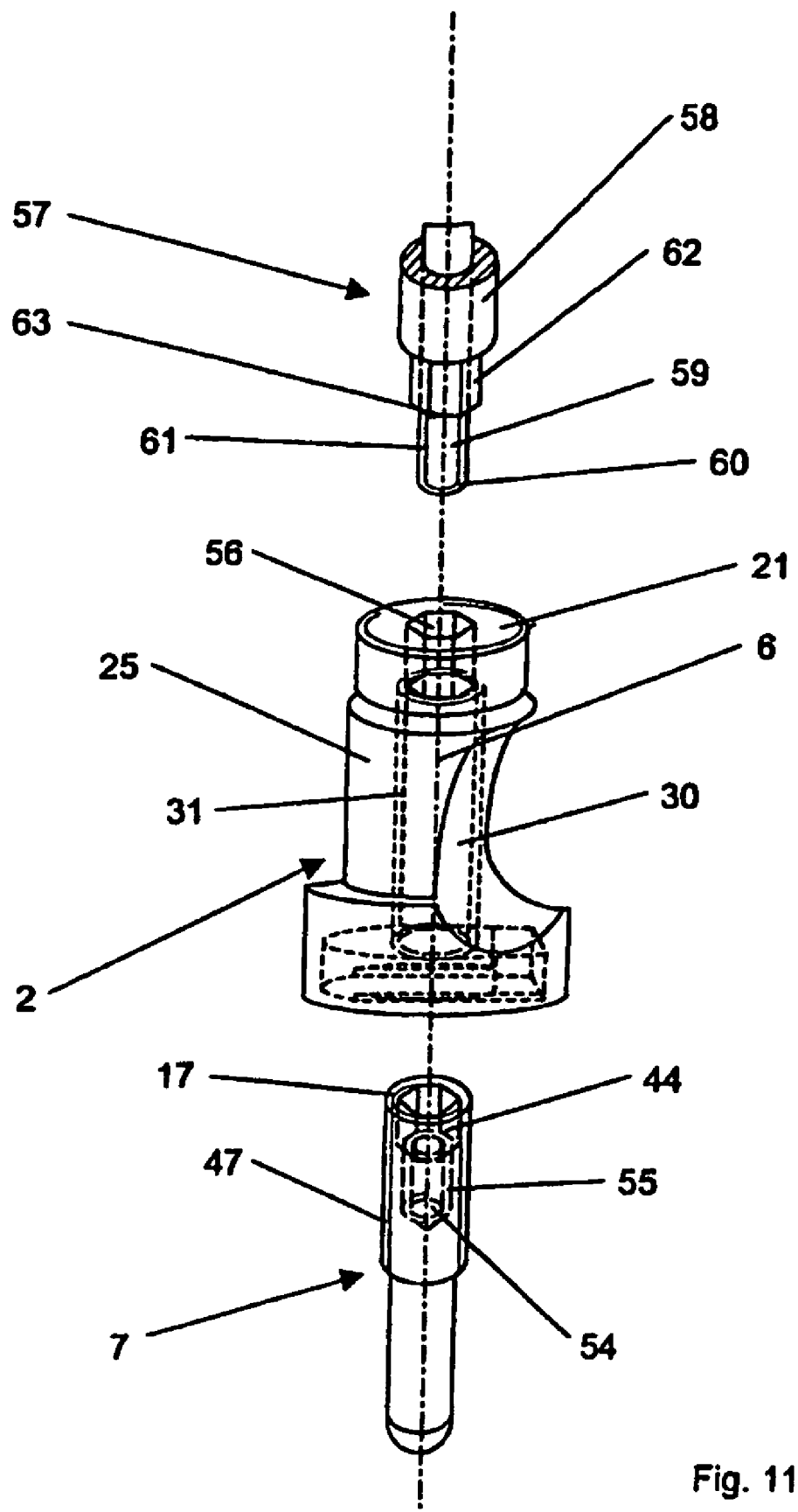
FIG. 11 shows an exploded representation of a part of an embodiment of the inventive device together with the fastening device.

As shown in FIG. 11, the device may include a second member 2 which is configured as a connecting part 25, clamping means 7 and a fastening device 57. As shown, the fastening device 57 may include a sleeve-like holder 58 and a threaded bolt 59, which can be moved coaxially along the central axis 6 of the holder 58. At its front end 63, the holder 58 has a hexagon drive 62, which is parallel to the central axis 6, and which is sized and configured to mate with a complementary hexagon socket 56 formed on the rear end 21 of the connecting part 25. At its front end 60, coaxially with the central axis 6, the threaded bolt 59 may include external threads 61, so that the threaded bolt 59 may threadedly engage the complementary internal threads 55 formed in the borehole 54, which penetrates from the rear end 17 of the clamping means 7 coaxially with the central axis 6 so that the clamping means may be connected with the fastening device 57.

The clamping means 7, which, as shown, is provided with an external thread 47 extending axially from the rear end 17, may threaded engage the complementary internal threads 31 formed in the central borehole 30 of the connecting part 25. Furthermore, in the rear end 17, coaxial with the central axis 6, the clamping means 7 may include means 44 for accommodating a screwdriver, a hex-driver, etc. As shown, the hexagon socket may include a cross-sectional dimension, which corresponds to the external diameter of the internal thread 55.

Similarly, the hexagon socket 56, mounted at the rear end 21 of the connecting part 25 coaxially with the central axis 6 in the central borehole 30, may have a cross-sectional dimension, which corresponds to the internal diameter of the internal thread 31 formed in the central borehole 30.

The present invention has been described in connection with the preferred embodiments. These embodiments, however, are merely for example and the invention is not restricted thereto. It will be understood by those skilled in the art that other variations and modifications can easily be made within the scope of the invention as defined by the appended claims, thus it is only intended that the present invention be limited by the following claims.

We claim:

1. A spinal implant device comprising:
   a bone fixation member having a spherically-shaped head, a fixation section extending from the head and attachable to bone, and a central axis;
   the head having a center lying on the central axis and having a depression in the top of the head, the depression having a spherically-shaped surface having a center lying on the central axis that coincides with the head center;
   a connection member having a central axis, an upper portion, a lower portion, and a bore extending through the upper and lower portions coaxial with the central axis of the connection member, the bore including internal threads within the upper portion;
   the lower portion having a cavity concentric with the central axis of the connection member, the cavity being in communication with the bore, and the lower portion having an opening for the passage therethrough of the fixation section, the cavity having a taper at the opening that forms a spherically-shaped support for the head of the bone fixation member, the spherically-shaped support forming a center;
   the upper portion having a channel formed therein in a peripheral side surface of the connection member for receiving a longitudinal rod, the channel having a channel axis disposed transversely to the central axis of the connection member, an opening of the channel facing radially outward from the peripheral side surface and away from the lower portion, the channel opening being disposed transversely to the central axis of the connection member and transversely to the channel axis;
   a covering cap having a tab parallel to the channel axis for laterally surrounding at least a portion of a longitudinal rod received in the channel, the covering cap being sized and configured to slidably engage an outer surface of the upper portion of the connection member; and
   a clamping member extending within the bore and the cavity of the connection member, the clamping member having a front end receivable in the depression and having a back end, the back end including external threads for engaging the threads formed in the bore of the connection member, the clamping member operative to clamp the head of the bone fixation member against the spherically-shaped support to lock the bone fixation member to the connection member;
   wherein the central axis of the connection member and the channel axis are laterally offset from each other by a distance A so that an outer surface of a longitudinal rod received in the channel is separated from an outer surface of the clamping member by the peripheral side surface of the connection member.

2. The device of claim 1 further comprising mounting means for securing a longitudinal rod received in the channel, wherein the connection member has an external thread at its upper portion and the mounting means is a nut having an internal thread sized and configured to threadably engage the external threads at the upper portion such that the mounting means engages the covering cap to secure the longitudinal rod in the channel.

3. The device of claim 1 wherein the channel axis is offset laterally and longitudinally from the head center.

4. The device of claim 1 wherein the clamping member is axially movable in the bore.

5. The device of claim 1 wherein the front end of the clamping member has a tip concentric with the central axis of the connection member.

6. The device of claim 1 wherein the front end of the clamping member has a flat surface orthogonal to the central axis of the connection member.

7. The device of claim 1 wherein the front end of the clamping member has a spherical configuration with a center coinciding with the center of the depression when the clamping member locks the bone fixation member to the connection member.

8. The device of claim 1 wherein the head of the bone fixation member has two flat perimeter sides opposite each other that enable the bone fixation member to be inserted into the connection member through the opening of the cavity from the lower portion of the connection member.

\* \* \* \* \*